United States Patent [19]

Teves

[11] Patent Number: 5,577,499
[45] Date of Patent: Nov. 26, 1996

[54] BLOOD ANALYZER

[76] Inventor: Leonides Y. Teves, 623-39th St. West, Bradenton, Fla. 34205

[21] Appl. No.: 317,074

[22] Filed: Oct. 3, 1994

[51] Int. Cl.$^6$ .............................. A61B 5/00; G01N 33/49
[52] U.S. Cl. .......................... 128/632; 128/635; 436/63; 436/68
[58] Field of Search ...................... 128/632, 634, 128/635, 637, 765, 760, 766; 204/403, 415; 436/63, 68; 73/19.1, 53.01

[56] References Cited

U.S. PATENT DOCUMENTS

| | | | |
|---|---|---|---|
| 3,910,256 | 10/1975 | Clark et al. | 128/635 |
| 4,608,996 | 9/1986 | Brown | 128/765 |
| 4,791,932 | 12/1988 | Margules | 128/632 |
| 4,961,833 | 9/1990 | Sakai et al. | 204/403 |
| 4,974,592 | 12/1990 | Branco | 128/635 |
| 5,046,496 | 9/1991 | Betts et al. | 128/635 |
| 5,089,421 | 2/1992 | Dieffenbach | 128/632 |
| 5,225,064 | 7/1993 | Henkens et al. | 204/403 |
| 5,244,561 | 9/1993 | Calzi et al. | 204/403 |

Primary Examiner—Angela D. Sykes
Assistant Examiner—Eric F. Winakur
Attorney, Agent, or Firm—Joseph C. Mason, Jr.; Louise A. Foutch

[57] ABSTRACT

A blood analyzer includes a display means that visually informs operating room personnel of the instantaneous condition of a patient's blood. Arterial or central venous tubing connects the analyzer to a blood vessel, either arterial, venous, or both, of the patient. In a first embodiment, a plurality of sensor means are positioned within a primary chamber of the analyzer. In a second embodiment, a secondary chamber in valved fluid communication with the primary chamber enables introduction of blood thereinto and a port is provided for entry of a syringe needle so that reactants may be introduced into the secondary chamber so that an additional test may be performed. In a third embodiment, the primary chamber is in valved fluid communication with a conventional pressure transducer.

8 Claims, 3 Drawing Sheets

BLOOD ANALYZER

BACKGROUND OF THE INVENTION

1. Field of the Invention

This invention relates, generally, to medical devices. More particularly, it relates to a miniature blood analyzer.

2. Description of the Prior Art

In addition to monitoring the vital signs of a patient under anesthesia during surgery, a number of other parameters are monitored as well. For example, the respective amounts of sodium, potassium, carbon dioxide, hematocrit-hemoglobin, and oxygen in a patient's blood are also monitored because such amounts must remain within certain critical limits.

The conventional way of monitoring the sodium, potassium, etc. content of a patient's blood is to take a blood sample from the patient, send it to the hospital's lab, and await the results of the analysis. Typically, the time delay between the taking of the blood sample and the delivery of the results to the surgical team is about forty five minutes in most hospitals. This is an unacceptably long time, however, because unacceptable levels of hematocrit-hemoglobin, sodium, etc., may be life threatening and the patient may not be strong enough to survive until the lab results are delivered. If a patient does survive the long wait, the needed action can be taken to reduce the arterial carbon dioxide content, for example, by changing the settings on a ventilator, etc., but another long wait must be endured before the next round of lab results are recived to indicate whether or not the patient is responding to the remedy. For a complex operation that requires many hours to complete, the number and spacing of lab reports is sometimes simply too few and far apart to be of significant value.

Information concerning the patient's condition is particularly critical when a patient is hemorraghing or in any other situation where transfusion of large amounts of blood is occuring. Physicians attending such highly unstable patients cannot long await lab results.

What is needed, then, is an improved means for analyzing a patient's blood. The improved means should substantially eliminate the forty five minute or more wait between the taking of a blood sample and the lab results. The improved means should be able to perform all of the tests typically performed by a lab, and it should be able to promptly inform the operating team of the lab results.

However, in view of the prior art as a whole at the time the present invention was made, it was not obvious to those of ordinary skill in this art how the needed means could be provided.

SUMMARY OF THE INVENTION

The present invention represents a revolutionary development in the art of health care. In effect, the laboratory is brought into the operating room, and the long wait for lab results of blood analysis is eliminated. The novel device provides almost instantaneous laboratory results to the surgical team, enabling them to apply appropriate remedies in a timely manner.

The novel device includes a first hollow chamber having a plurality of sensors positioned therewithin. Each sensor is connected to a display means so that signals from each sensor are used to drive a display means. Thus, operating room personnel merely need to observe the display means to learn the analysis of the patient's blood.

In a first embodiment of the invention, a catheter such as a high pressure arterial tube or a central venous tube is extended from an arterial source or a central venous source, respectively, or both, to the hollow chamber; a valve in the tube admits blood from said source into the chamber when opened. The sensors are immersed within the blood, and measure its sodium, potassium, carbon dioxide, and oxygen content. A pH meter, a blood sugar sensor, and other sensors may be provided as well. The sensors, which are commercially available and which are used in laboratories, generate signals in a minute or so and output those signals to the display means. Thus, the surgical team knows the condition of the patient's blood within a minute or so of opening the valve in the tubing.

In a second embodiment, an imperforate partition wall is positioned within the hollow chamber to divide it into a first hollow chamber and a second hollow chamber, and a valve is positioned in said partition wall to enable selective fluid communication between said first and second chambers. The aforementioned sensors are positioned within the first chamber and an additional sensor is positioned within the second chamber. The arterial tubing is extended from the patient to the first chamber as in the first embodiment. A normally closed port is positioned in a preselected wall of the second chamber to admit the needle of a syringe therethrough so that the valve in the partition wall may be opened to admit blood into said second chamber, and a syringe may be used to inject reagents into the blood in the second chamber so that the sensor in the second chamber can detect the hematocrit or hemoglobin content of the blood and generate the information-carrying signals to the display means.

In a third embodiment, the primary hollow chamber is placed into valved fluid communication with a conventional pressure transducer; the valved high pressure arterial tubing is placed between the arterial or central venous source (or both) and the pressure transducer so that blood is admitted into the pressure transducer when the valve is opened so that the patient's blood pressure may be measured. A valve is positioned between the first chamber of the novel miniature lab and the pressure transducer so that blood may be admitted from the pressure transducer into the primary chamber as desired. The valve between the primary and secondary chambers may also be opened if the hamatocrit or hemoglobin tests are to be performed.

A fourth embodiment includes the secondary chamber of the second embodiment in conjunction with the primary chamber and the pressure transducer.

Thus it is understood that a primary object of the present invention is to provide a miniature laboratory directly connectable to a patient so that the operating team need not await analysis reports from a remote laboratory.

A closely related object is to provide the miniature lab in differing configurations to enhance its versatility.

These and other important objects, features and advantages of the invention will become apparent as this description proceeds.

The invention accordingly comprises the features of construction, combination of elements and arangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
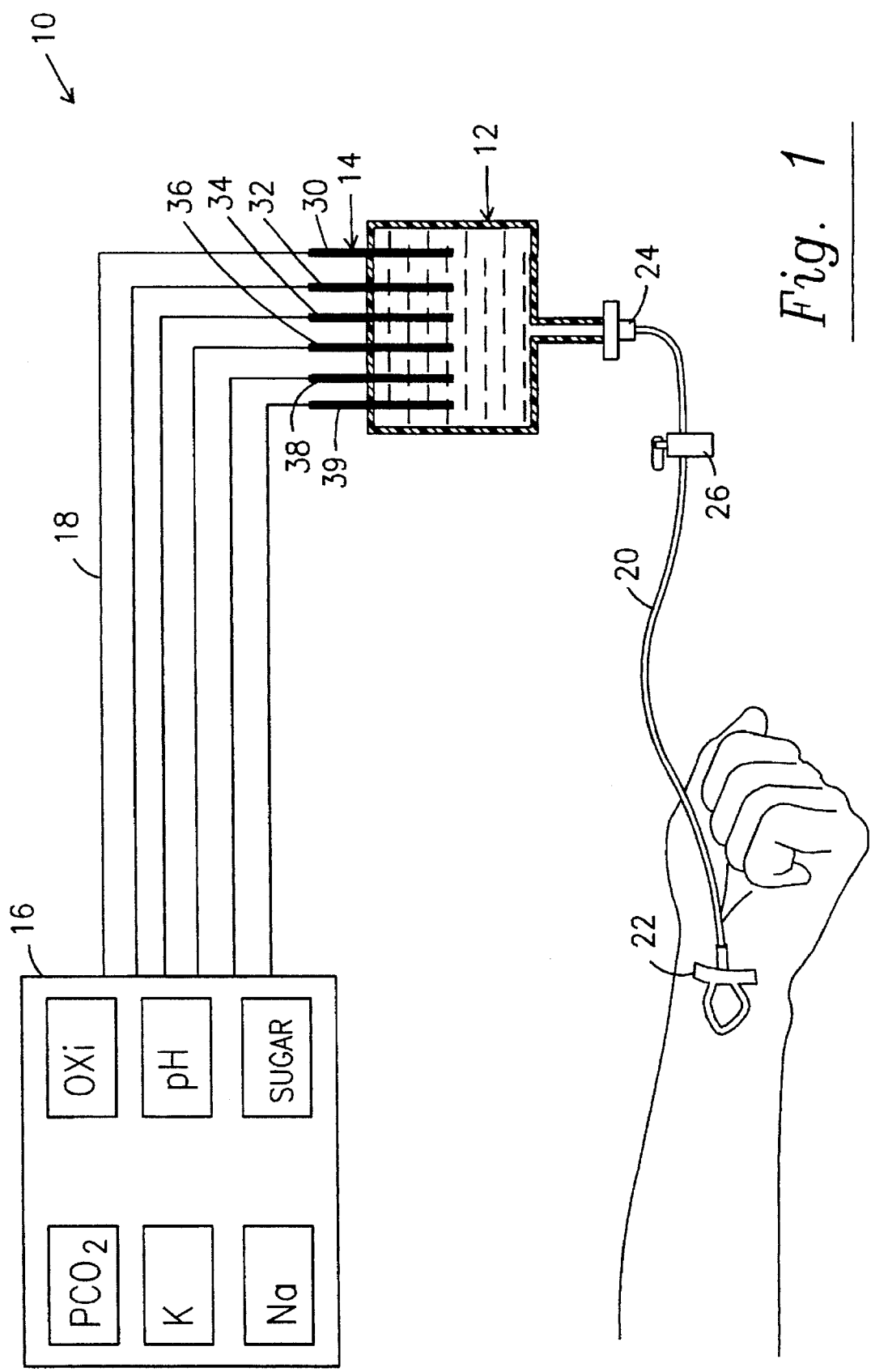
FIG. 1 is a side elevational view of a first embodiment of the invention.

Referring now to FIG. 1, it will there be seen that a first illustrative embodiment of the invention is denoted as a whole by the reference numeral 10.

Novel device 10 includes a chamber 12 of hollow construction, at least a first sensor means 14 disposed within said chamber, a display means 16 exterior to said chamber, means 18 electrically connecting said first sensor means and said display means so that a signal generated by said sensor means is delivered to said display means, a tubing means 20 having a leading end 22 adapted for fluid communication with a patient's blood vessel and a trailing end 24 in fluid communication with chamber 12, and an open-closed valve means 26 disposed in tubing means 20 for selectively controlling entry of blood into chamber 12. Note that blood flowing under an impulse provided by the patient's heart (or a heart machine) enters the chamber through an opening formed in the bottom wall of said chamber. Tubing 20 may be arterial tubing (if connected to an arterty) or central venous tubing (if connected to a central vein). Display means 16 displays a numerical value representing a parameter of the patient's blood as measured by first sensor means 14 so that a physician observing display means 16 is informed of said parameter.

In a preferred embodiment, chamber 12 may house a plurality of sensor means, such as a sodium sensor 30, a potassium sensor 32, a carbon dioxide sensor 34, an oxygen sensor 36, and a pH sensor 38. Embellishment of this invention by the addition of additional sensors such as a blood sugar sensor 39 or by the substitution of different sensors or combinations thereof is within the scope of this invention, of course.

In a second embodiment, chamber 12 is subdivided into a primary chamber 40 and a secondary chamber 42. More particularly, the second embodiment, shown in FIG. 2, includes partition wall 44 disposed within said chamber, valve means 46 disposed in said partition wall 44 for selectively controlling flow of blood from said primary chamber 40 into said secondary chamber 42, at least one secondary sensor means 48 disposed within said secondary chamber 42, means 47 electrically connecting said at least one secondary sensor means 48 to an auxiliary display means 49 so that a signal generated by said at least one secondary sensor means is delivered to said auxiliary display means, and a port means 50 mounted on said secondary chamber that enables introduction of reactants into said secondary chamber by a syringe means 51, said reactants reacting with blood in said secondary chamber to determine preselected chemical characteristics of said blood.

In this embodiment, sensor means 48 may be provided in the form of a sensor that detects the hematocrit content of blood after the blood has been reacted with said reactants. The addition or substitution of other sensors, such as hemoglobin sensors, in secondary chamber 42 is also within the scope of this invention. Moreover, auxiliary display means 49 could be combined with primary display means 16.

Figure 2:
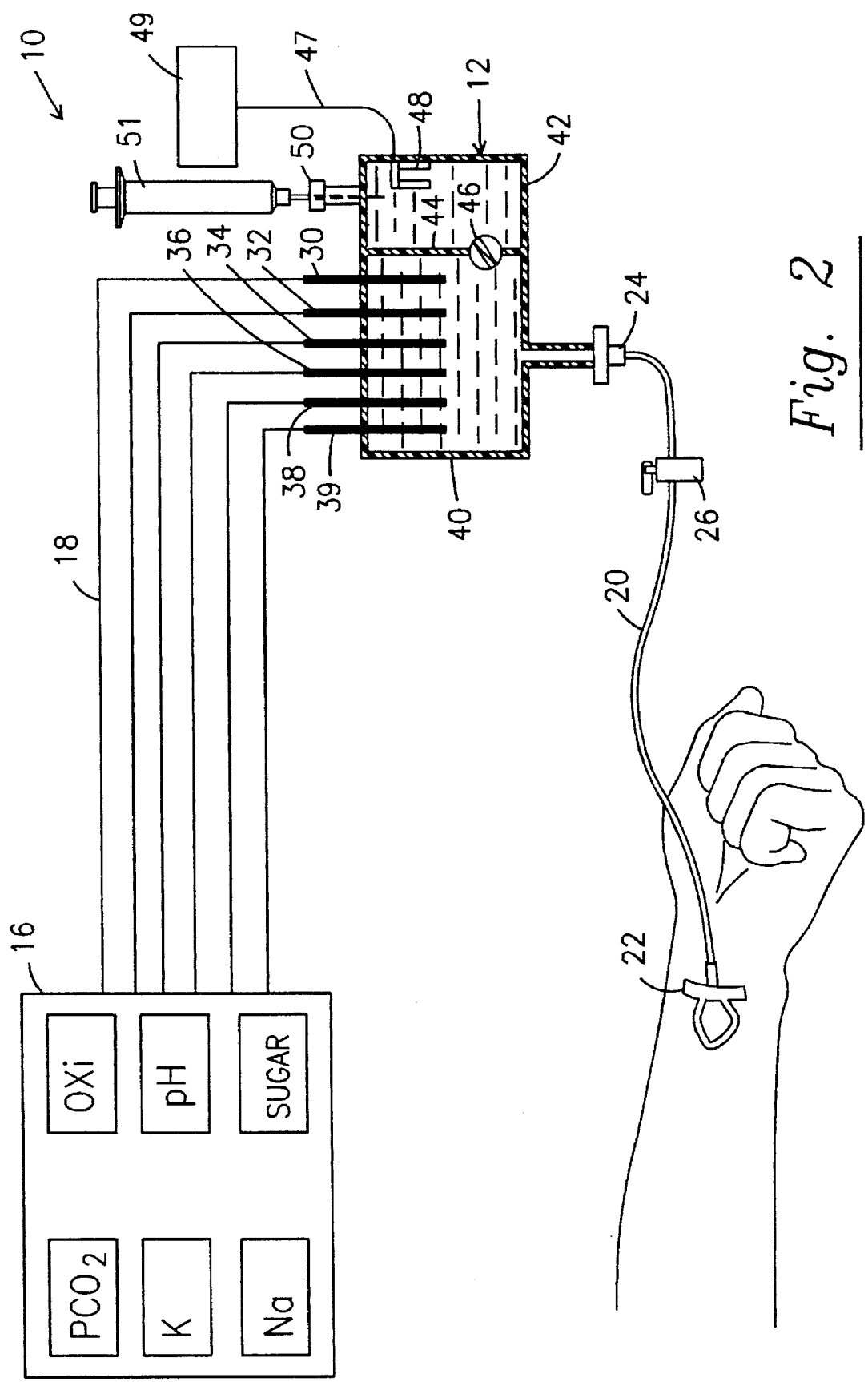
FIG. 2 is a side elevational view of a second embodiment of the invention
Figure 3:
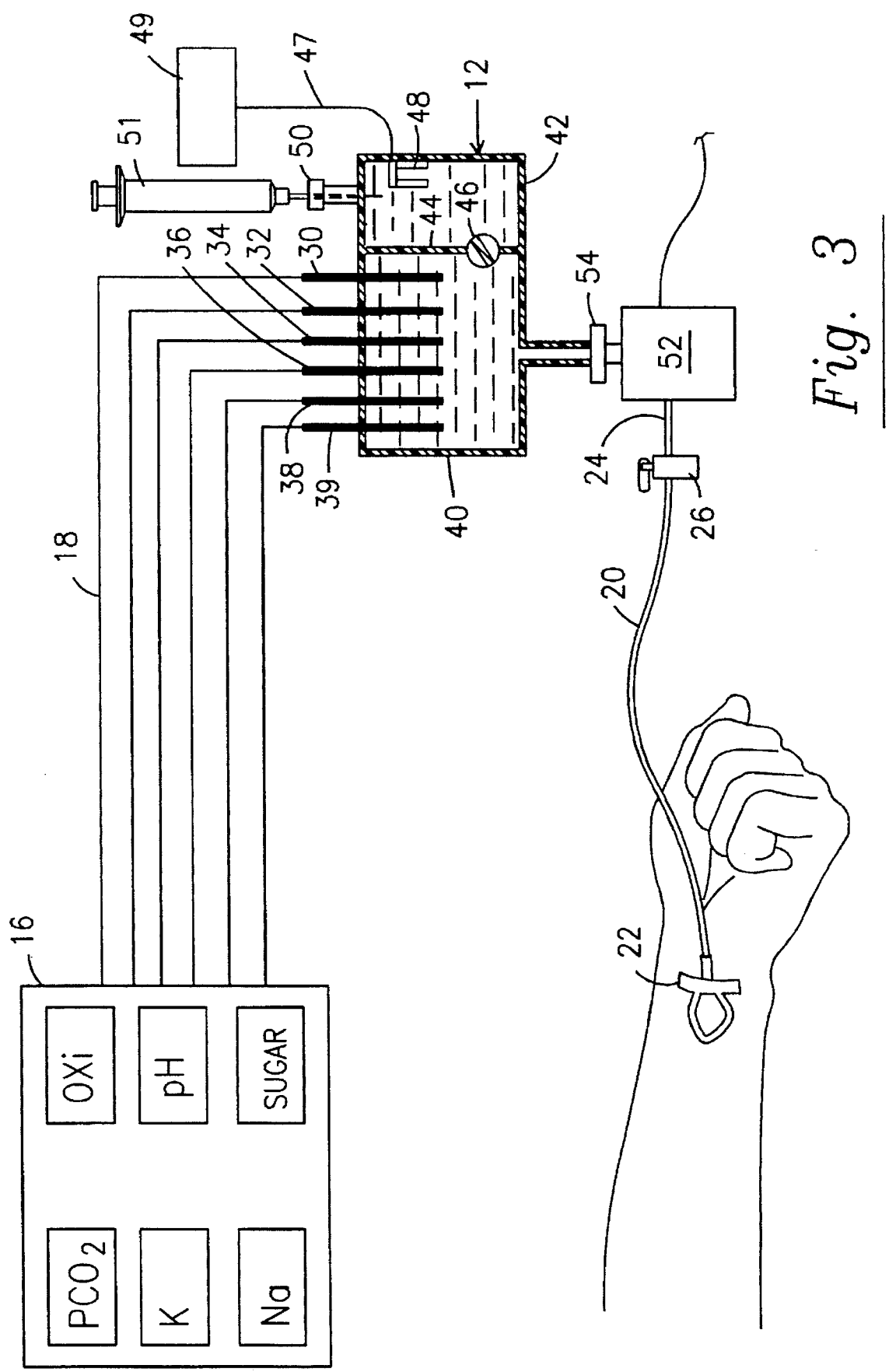
FIG. 3 is a side elevational view of a third embodiment of the invention.

FIG. 3 is a composite view depicting both the third and fourth embodiments of this invention. Specifically, in a third embodiment of the invention, the embodiment of FIG. 1 is connected in fluid communication to a conventional pressure transducer 52, and in a fourth embodiment, the embodiment of FIG. 2 is connected in fluid communication to said conventional pressure transducer. Thus, FIG. 3 includes tubing means 20 having leading end 22 adapted for fluid communication with an arterial or central venous source and a trailing end 24 adapted for fluid communication with said pressure transducer 52. First valve means 26 is disposed in said tubing means 20 for selectively controlling entry of blood into pressure transducer 52, and a second valve means 54 is disposed between said pressure transducer and chamber 12 for controlling selective entry of blood from said pressure transducer into the chamber. The other parts of this embodiment are the same as in the earlier embodiments. FIG. 3 also includes secondary chamber 42 and its related parts to depict the fourth embodiment as well as aforesaid.

The sensors may be provided in the form of removably mounted dipsticks so that they may be discarded after use, or autoclaved and reused. They may also be permanently secured into their respective positions, and flushing and rinsing means may be provided for flushing the unit after use and rinsing it so that it may be reused.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A device for analyzing blood, comprising:

a chamber of hollow construction;

said chamber adapted to hold a predetermined quantity of a patient's blood;

a first sensor means disposed within said chamber;

said first sensor means having a first end immersed within blood in said chamber when said predetermined quantity of said patient's blood is within said chamber;

a display means exterior to said chamber;

means electrically connecting an unimmersed second end of said first sensor means and said display means so that a signal generated by said first sensor means is delivered to said display means;

a tubing means having a leading end adapted for fluid communication with a patient's blood vessel and a trailing end in fluid communication with said chamber;

an open-closed valve means disposed in said tubing means for selectively controlling entry of blood into said chamber;

said trailing end of said tubing means being in fluid communication with said chamber through an opening formed in a bottom wall of said chamber, said chamber filling with blood when said open-closed valve means is in an open configuration, said blood flowing into said chamber under an impulse provided by said patient's blood pressure;

said display means displaying a numerical value representing a parameter of said patient's blood as measured by said first sensor means;

whereby an operating team need not await results of laboratory blood tests during a surgical operation.

2. A device for analyzing blood, comprising:

a chamber of hollow construction;

said chamber adapted to hold a predetermined quantity of a patient's blood;

a plurality of sensor means disposed within said chamber;

each sensor means of said plurality of sensor means having a first end immersed within blood in said chamber when said predetermined quantity of said patient's blood is within said chamber;

a display means exterior to said chamber;

means electrically connecting an unimmersed second end of each sensor means of said plurality of sensor means and said display means so that signals generated by each sensor means of said plurality of sensor means is delivered to said display means;

a tubing means having a leading end adapted for fluid communication with a patient's blood vessel and a trailing end in fluid communication with said chamber;

an open-closed valve means disposed in said tubing means for selectively controlling entry of blood into said chamber;

said trailing end of said tubing means being in fluid communication with said chamber through an opening formed in a bottom wall of said chamber, said chamber filling with blood when said open-closed valve means is in an open configuration, said blood flowing into said chamber under an impulse provided by said patient's blood pressure;

said display means displaying a plurality of numerical values representing a plurality of parameters of said patient's blood as measured by said plurality of sensor means;

whereby an operating team need not await results of laboratory blood tests during a surgical operation.

3. The device of claim 2, wherein said plurality of sensor means includes a sodium sensor.

4. The device of claim 2, wherein said plurality of sensor means includes a potassium sensor.

5. The device of claim 2, wherein said plurality of sensor means includes a carbon dioxide sensor.

6. The device of claim 2, wherein said plurality of sensor means includes an oxygen sensor.

7. The device of claim 2, wherein said plurality of sensor means includes a pH sensor.

8. The device of claim 2, wherein said plurality of sensor means includes a blood sugar sensor.

* * * * *